United States Patent
Greene

(10) Patent No.: US 6,529,774 B1
(45) Date of Patent: Mar. 4, 2003

(54) EXTRADURAL LEADS, NEUROSTIMULATOR ASSEMBLIES, AND PROCESSES OF USING THEM FOR SOMATOSENSORY AND BRAIN STIMULATION

(75) Inventor: David A. Greene, Ft. Wayne, IN (US)

(73) Assignee: NeuroPace, Inc., Mountain View, CA (US)

( * ) Notice: Subject to any disclaimer, the term of this patent is extended or adjusted under 35 U.S.C. 154(b) by 24 days.

(21) Appl. No.: 09/711,663

(22) Filed: Nov. 9, 2000

(51) Int. Cl.[7] .............................................. A61B 5/0478
(52) U.S. Cl. ........................ 600/545; 600/378; 607/45; 607/116
(58) Field of Search .................... 607/45, 116; 600/373, 600/378, 544, 545

(56) References Cited

U.S. PATENT DOCUMENTS

| | | |
|---|---|---|
| 3,531,561 A | 9/1970 | Trehu |
| 3,565,066 A | 2/1971 | Roaf et al. |
| 3,636,956 A | 1/1972 | Schneider |
| 3,960,151 A | 6/1976 | Kuhn |
| 3,993,046 A | 11/1976 | Fernandez et al. |
| 4,429,690 A | 2/1984 | Angelino-Pievani |
| 4,523,591 A | 6/1985 | Kaplan et al. |
| 4,566,464 A | 1/1986 | Piccone et al. |
| 4,702,254 A | 10/1987 | Zabara |
| 4,735,208 A | 4/1988 | Wyler et al. |
| 4,781,183 A | 11/1988 | Casey et al. |
| 4,867,164 A | 9/1989 | Zabara |
| 4,903,702 A | 2/1990 | Putz |
| 4,905,680 A | 3/1990 | Tunc |
| 4,979,511 A | 12/1990 | Terry, Jr. |
| 5,025,807 A | 6/1991 | Zabara |
| 5,031,618 A | 7/1991 | Mullett |
| 5,097,835 A | 3/1992 | Putz |
| 5,129,903 A | 7/1992 | Luhr et al. |
| 5,154,172 A | 10/1992 | Terry, Jr. et al. |

(List continued on next page.)

FOREIGN PATENT DOCUMENTS

| | | |
|---|---|---|
| DE | 8528003 | 2/1986 |
| DE | 8706912 | 10/1987 |
| DE | 3701765 C1 | 6/1988 |

(List continued on next page.)

OTHER PUBLICATIONS

Andriano, K.P. et al. (1994). "Processing and Characterization of Absorbable Polyactide Polymers for Use in Surgical Implants," *Journal of Applied Biomaterials* 5: 133–140.

(List continued on next page.)

*Primary Examiner*—John Rivell
(74) *Attorney, Agent, or Firm*—Morrison & Foerster LLP

(57) ABSTRACT

This is directed to a neurostimulator assembly that is preferably implantable and is suitable for treating epilepsy and other neurological disorders. The assembly includes inventive leads that are suitable both for providing electrical somatosensory stimulation, extradurally applied, as well as electrical stimulation that is applied to the central nervous system. The leads are preferably also suitable for sensing electrical signals in the brain. The invention includes processes of using the neurostimulator and its leads. The neurostimulator may independently provide a variety of different electrical stimulation, e.g., non-responsive electrical stimulation signals applied to the central nervous system to reduce the likelihood of a seizure or other undesirable neurological even from occurring, electrical stimulation signals applied to the central nervous system when the neurostimulator determines that epileptiform waveforms are impending or extant, and extradural electrical somatosensory stimulation signals. The responsive electrical stimulation signal or signals are intended to terminate epileptiform activity, e.g., to desynchronize abnormally synchronous brain electrical activity.

21 Claims, 4 Drawing Sheets

U.S. PATENT DOCUMENTS

| | | |
|---|---|---|
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,303 A | 12/1993 | Wernicke et al. |
| 5,293,879 A | 3/1994 | Vonk et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,330,515 A | 7/1994 | Rutecki et al. |
| 5,335,657 A | 8/1994 | Terry, Jr. et al. |
| 5,349,962 A | 9/1994 | Lockard et al. |
| 5,351,394 A | 10/1994 | Weinberg |
| 5,372,598 A | 12/1994 | Luhr et al. |
| 5,413,577 A | 5/1995 | Pollock |
| 5,474,547 A | 12/1995 | Aebischer et al. |
| 5,522,863 A | 6/1996 | Spano et al. |
| 5,531,778 A | 7/1996 | Maschino et al. |
| 5,540,730 A | 7/1996 | Terry, Jr. et al. |
| 5,540,734 A | 7/1996 | Zabara |
| 5,560,358 A * | 10/1996 | Arnold et al. ............... 128/642 |
| 5,569,250 A | 10/1996 | Sarver et al. |
| 5,571,150 A | 11/1996 | Wernicke et al. |
| 5,604,204 A | 2/1997 | Ammann et al. |
| 5,676,655 A | 10/1997 | Howard, III et al. |
| 5,683,422 A | 11/1997 | Rise |
| 5,702,429 A | 12/1997 | King |
| 5,707,396 A | 1/1998 | Benabid |
| 5,707,400 A | 1/1998 | Terry, Jr. et al. |
| 5,711,316 A | 1/1998 | Elsberry et al. |
| 5,713,923 A | 2/1998 | Ward et al. |
| 5,716,377 A | 2/1998 | Rise et al. |
| 5,735,814 A | 4/1998 | Elsberry et al. |
| 5,752,979 A | 5/1998 | Benabid |
| 5,782,798 A | 7/1998 | Rise |
| 5,792,186 A | 8/1998 | Rise |
| 5,800,474 A | 9/1998 | Benabid et al. |
| 5,814,092 A | 9/1998 | King |
| 5,832,932 A | 11/1998 | Elsberry et al. |
| 5,833,709 A | 11/1998 | Rise et al. |
| 5,843,093 A | 12/1998 | Howard, III |
| 5,843,148 A | 12/1998 | Gijsbers et al. |
| 5,857,987 A | 1/1999 | Hively et al. |
| 5,868,746 A | 2/1999 | Sarver et al. |
| 5,902,236 A | 5/1999 | Iversen |
| 5,913,882 A | 6/1999 | King |
| 5,928,272 A | 7/1999 | Adkins et al. |
| 5,938,689 A | 8/1999 | Fischell et al. |
| 5,978,702 A | 11/1999 | Ward et al. |
| 5,995,868 A | 11/1999 | Dorfmeister et al. |
| 6,006,124 A | 12/1999 | Fischell et al. |
| 6,016,449 A | 1/2000 | Fischell et al. |
| 6,018,682 A | 1/2000 | Rise |
| 6,024,702 A | 2/2000 | Iversen |
| 6,066,163 A | 5/2000 | John |
| 6,091,979 A * | 7/2000 | Madsen ................... 600/378 X |
| 6,094,592 A | 7/2000 | Yorkey et al. |
| 6,094,598 A | 7/2000 | Elsberry et al. |
| 6,095,148 A | 8/2000 | Shastri et al. |
| 6,109,269 A | 8/2000 | Rise et al. |
| 6,109,270 A | 8/2000 | Mah et al. |
| 6,113,553 A | 9/2000 | Chubbuck |
| 6,161,045 A | 12/2000 | Fischell et al. |
| 6,205,359 B1 * | 3/2001 | Boveja ......................... 607/45 |
| 6,230,049 B1 * | 5/2001 | Fischell et al. ............. 600/544 |
| 6,354,299 B1 * | 3/2002 | Fischell et al. ............. 128/899 |

FOREIGN PATENT DOCUMENTS

| | | |
|---|---|---|
| EP | 0 195 455 A1 | 9/1986 |
| EP | 0 276 153 A3 | 7/1988 |
| EP | 0 276 153 A2 | 7/1988 |
| EP | 0 290 138 A3 | 11/1988 |
| EP | 0 290 138 A2 | 11/1988 |
| EP | 0 291 632 A1 | 11/1988 |
| EP | 0 347 658 A1 | 12/1989 |
| EP | 0 195 455 B1 | 2/1990 |
| EP | 0 491 983 A1 | 7/1992 |
| EP | 0 291 632 B1 | 7/1993 |
| EP | 0 347 658 B1 | 9/1993 |
| EP | 0 491 983 B1 | 3/1996 |
| EP | 0 290 138 B1 | 7/1996 |
| EP | 0 291 632 B2 | 8/1998 |
| GB | 2140523 A | 11/1984 |

OTHER PUBLICATIONS

Chkhenkeli, S.A. and Chkhenkeli, I.S. (1997). "Effects of Therapeutic Stimulation of Nucleus Caudatus on Epileptic Electrical Acticity of Brain Activity o Brain in Patients woth Intractable Epilepsey," *Stereotact Funct Neurosurg* 69:221–224.

Cooper, I.S. et al. (1974). "The Effect of Chronic Stimulation of Cerebellar Cortex on Epilepsy in Man," *In The Cerebellum, Epilepsy, and Behavior*. Cooper, I.S. et al., eds., Plenum Press:New York, pp.119–171.

Cooper, I.S. et al. (1977/78). "Safety and Efficacy of Chronic Cerebellar Stimulation," *Appl. Neurophysiol.* 40:124–134.

Cooper, I.S. and Upon, A.R.M. (1978). "Effects of Cerebellar Stimulation on Epilepsy, the EEG and Cerebral Palsy in Man," *In Contemporary Clinical Neurophysiology (EEG Suppl. No. 34)*. Cobb, W.A. et al., eds., Elsevier Scientific Publishing: Amsterdam, pp. 349–354.

Davis, R. and Emmonds, S.E. (1992). "Cerebellar Stimulation for Seizure Control: 17–Year Study," *Stereotact. Funct. Neurosung.* 58:200–208.

Eppley, B.L. and Sadove, A.M. (1992). "Effects of Resorbable Fixation on Craniofacial Skeletal Growth: A Pilot Experimental Study," *Journal of Craniofacial Surgery* 3(4):190–196.

Gerlach, K.L. (1993). "In–vivo and Clinical Evaluations of Poly(L–lactide) Plates and Screws for Use in Maxillofacial Traumatology," *Clinical Materials* 13:21–28.

Gotman, J. (1999). "Automatic Detection of Seizures and Spikes," *Journal of Clinical Neurophysiology* 16(2):130–140.

Osorio, I. et al (1995). "Method for Accurate Automated Real–Time Seizure Detection," *Epilepsia*36(supplement 4):4, Abstract No. 1.04.

Qu, H. and Gotman, J. (1995). "A Seizure Warning System for Long–Term Epilepsy Monitoring," *Neurology* 45:2250–2254.

Salyer. K.E. et al. (1994). "A Comparative Study of theEffects of Biodegradable and Titanium Plating Systems on Cranial Growth and Structure: Experimental Study in Beagles," *Plastic and Recostructive Surgery* 93(4):705–713.

Schiff, S.J. et al. (1994). "Controlling Chaos in the Brain," *Nature* 370:615–620.

Thaller, S.R. et al. (1992). "Use of Biodegradable Plates and Screws in a Rabbit Model," *Journal of Craniofacial Surgery* 2(4):168–173.

Velasco, F. et al. (1995). "Electrical Stimulation of the Centromedian Thalamic Nucleus in Control of Seizures: Long Term Studies," *Epilepsia* 36(1):63–71.

* cited by examiner

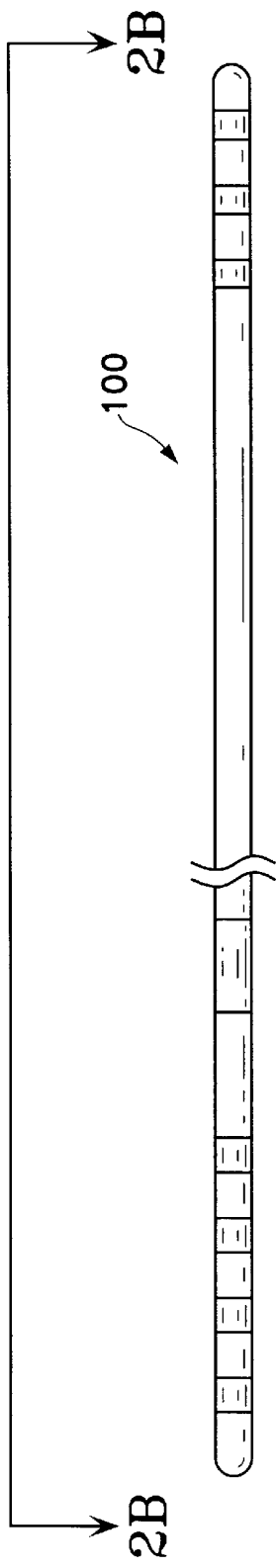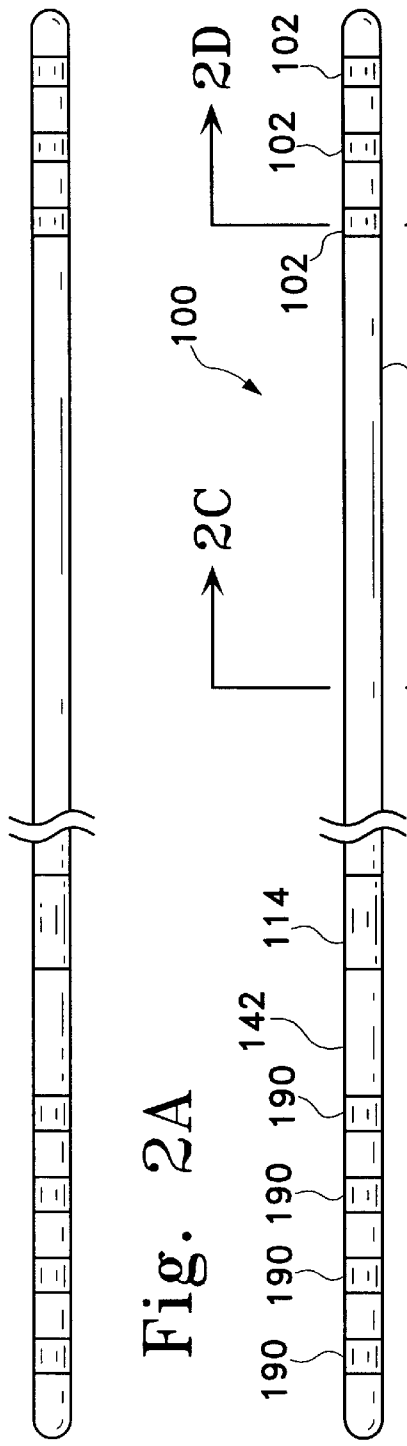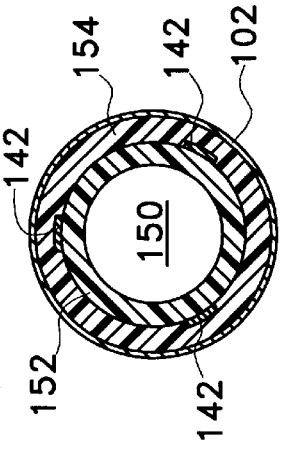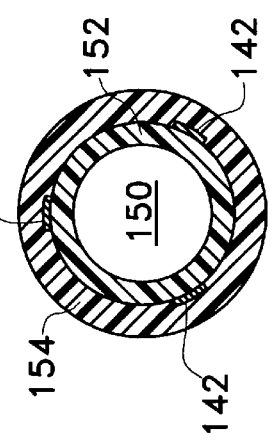
Fig. 2A
Fig. 2B
Fig. 2C
Fig. 2D

EXTRADURAL LEADS, NEUROSTIMULATOR ASSEMBLIES, AND PROCESSES OF USING THEM FOR SOMATOSENSORY AND BRAIN STIMULATION

FIELD OF THE INVENTION

This invention is directed to a neurostimulator that is preferably implantable and is suitable for treating epilepsy and other neurological disorders. The invention includes inventive leads that are suitable both for providing electrical somatosensory stimulation, extradurally applied, as well as electrical stimulation that is applied to the central nervous system. The leads are preferably also suitable for sensing electrical signals in the brain. The invention includes processes of using the neurostimulator and its leads.

The neurostimulator may independently provide a variety of different electrical stimulation, e.g., non-responsive electrical stimulation signals applied to the central nervous system to reduce the likelihood of a seizure or other undesirable neurological even from occurring, electrical stimulation signals applied to the central nervous system when the neurostimulator determines that epileptiform waveforms are impending or extant, and extradural electrical somatosensory stimulation signals.

The responsive electrical stimulation signal or signals are intended to terminate epileptiform activity, e.g., to desynchronize abnormally synchronous brain electrical activity.

BACKGROUND OF THE INVENTION

Epileptic seizures are characterized by hypersynchronous neuronal activity. Neurologists recognize a wide variety of seizures. Partial onset seizures begin in one part of the brain; general onset seizures arise throughout the entire brain simultaneously. When partial onset seizures progress to involve much of the brain, they are said to have "secondarily generalized." Some seizures result in the loss of conscious awareness and are termed "complex" seizures. So-called "simple" seizures may involve other symptoms, but consciousness is unimpaired. Seizure symptoms may include sensory distortions, involuntary movements, or loss of muscle tone. The behavioral features of seizures often reflect a function of the cortex where the abnormal electrical activity is found.

Physicians have been able to treat epilepsy by resecting certain brain areas by surgery and by medication. Brain surgery is irreversible, and is either ineffective or is associated with neural morbidity in a sizable percentage of cases. Medication is the most prevalent treatment for epilepsy. It is effective in over half of patients, but in the reminder of the patients, the medication is either ineffective in controlling seizures, or the patients suffer from debilitating side effects. A promising method of treating patients having epileptic seizures is electrical stimulation of the brain.

Since the early 1970's, electrical brain stimulators have been used which provide more or less constant stimulation, the stimulation largely being unrelated to detected electrical activity.

Electrical stimulation of the nervous system has been used to suppress seizures. A device is described in Cooper et al. for stimulation of the cerebellum. See, "The Effect of Chronic Stimulation of Cerebellar Cortex on Epilepsy and Man," I. S. Cooper et al in *The Cerebellum, Epilepsy and Behavior*, Cooper, Riklan and Snyder Edition, Pleman Press, N.Y. 1974. Others have utilized devices which stimulated the centro median nucleus of the thalamus. See, "Electrical Stimulation of the Centro Median Thalamic Nucleus in Control of Seizures: Long Term Studies." F. Valasco et al, *Epilepsia*, 36 (1): 63–71, 1995. Chaos Theory has been used to apply stimulation to a seizure focus in vitro to abort the seizure. See, S. Schiff et al, "Controlling Chaos in the Brain," *Nature*, Volume 370, Aug. 25, 1994.

Non-responsive electrical stimulation devices have been used for significant periods. The devices and procedures did not constitute a panacea, however. For instance, a 17 year follow-up study shown in Davis et al. ("Cerebellar Stimulation for Seizure Control 17 Year Study," Proceedings of the Meeting of the American Society for Stereotactic and Functional Neurosurgery, Pittsburgh, Pa., Jun. 16–19, 1991 and in Stereotact. Funct. Neurosurg. 1992; 58; 200–208) showed that less than one-half of the patients became seizure free, even though 85% showed some benefit.

Responsive brain stimulation, specifically electrical stimulation that is applied to the brain, has not yet been used to treat patients in long-term studies. This is true even though there are algorithms suitable for detection of the onset of an epileptic seizure. For instance, Qu et al provide an algorithm said to recognize patterns of electrical activity similar to those developed while recording an actual epileptic seizure. See, Qu et al., "A Seizure Warning System for Long-Term Epilepsy Monitoring, *Neurology*," 1995; 45:2250–2254. Similarly, Osorio, et al. have suggested an algorithm applied to signals from intracranial electrodes with good results. See Osorio, et al. "A Method For Accurate Automated Real-Time Seizure Detection," *Epilepsia*, Vol. 35, supplement 4, 1995.

Finally, in conjunction with direct brain tissue stimulation, electrical signals that are applied to regions of the body which are not neurological tissue, e.g., applied extradurally to the skin and particularly to the scalp, have been shown to be useful in delaying or preventing the onset of a seizure.

In applying the various electrical stimuli to the brain, a number of different electrode configurations are known.

U.S. Pat. Nos. 4,702,254, 4,867,164, and 5,025,807, each to Zabara, show a device for controlling or preventing involuntary movements such as caused by epileptic seizures. The device is made up of an electrical pulse generator, a positive electrode to be applied to a person's body, and a negative electrode to be placed adjacent the vagus nerve in that body.

U.S. Pat. No. 4,735,208, to Wyler et al., shows a subdural strip electrode for determining epileptogenic foci. The strip has a long, tapered proximal end portion terminating in a narrow tip from which a number of wires extend. This is said to allow withdrawal of the strip electrode without a substantial incision. Strip width and thickness are said to be such that the strip may be withdrawn after extended implantation without the need for surgery. In one variation, the central region of the strip is significantly reinforced.

U.S. Pat. No. 4,903,702, to Putz, shows an electrical brain-electrode device for increased accuracy in determining epileptogenic foci. This device has a dielectric base member and an array of electrodes mounted on that base member. Each of the electrodes has a separate wire for connection to a measurement device. The device preferably has radio-opaque regions adjacent to at least one of the electrodes such that the position of the electrodes with respect to the brain may be more readily determined by x-ray.

U.S. Pat. No. 5,097,835, also to Putz, shows a subdural electrode for determining epileptogenic foci. The device is said to have dielectric layers and at least one electrode disc placed between the layers. The disc includes a tab. The accompanying lead wire is folded over the outer segment of the tab so that the tab crimps the wire. The electrical and mechanical integrity of the connection is improved by wrapping the wire about the tab several times before crimping.

U.S. Pat. Nos. 5,702,429, 5,814,092, and 5,913,882, each to King, show a neural stimulation technique with feedback and further shows a variety of stimulating and recording leads (e.g., #10 in FIG. 1 discussed at column 2 beginning at line 21) and other embodiments shown in FIGS. 2–5. King shows (beginning at column 3, line 60) the manner of using the stimulating electrodes (18–21) and the recording electrodes (25–26). Generally, the placement of the electrodes is said to be "at sites adjacent electrically excitable tissue for control of conscious paresthesia into the painful area of a patient." The patent goes on to explain that: "electrically excitable tissue includes neural tissue intrinsic to the heart and other organs, a peripheral nerve, the spinal cord surface, the interior of the spinal cord, deep brain tissue, brain surface tissue, and neural ganglia." See, column 3, line 5 following.

U.S. Pat. No. 5,782,798, to Rise, shows a device for dispersing one or more drugs and/or electrical stimulation to treat eating disorders. The treatment is carried out with an implantable pump and a catheter having a proximal end coupled to the pump. The catheter may have stimulation electrodes (38 and 40 in FIG. 3). The stimulation electrodes may in some instances serve as reference electrodes as well.

U.S. Pat. No. 5,800,474, to Benabid et al., shows a method and apparatus for providing high frequency electrical stimulation pulses to the subthalamic nucleus to block neural activity in the subthalamic nucleus and reduce excitatory input to the substantia nigra which is said to lead to an overall reduction in occurrence of seizures. The device used there is a lead (22A in the Figure) having four stimulation electrodes (115) implanted into a portion of the basal ganglia of the brain.

U.S. Pat. No. 5,843,093, to Howard III, shows a dual purpose multi-electrode neuron-monitoring electrode assembly which may also be used to deliver drugs to the brain. The device is used particularly for selectively inactivating specific regions of the brain using ablative surgery. In addition, the device is used as a neural prosthetic device for the auditory cortex apparently to resolve deafness problems. The various devices of interest are generally shown in FIGS. 6 through 11B.

U.S. Pat. No. 5,843,148, to Gijsbers et al., shows a high resolution brain stimulation lead which is able to stimulate exclusively certain selected small neurological targets without damage to the involved brain tissue. The structure is best shown in FIGS. 2, 3A and 3B.

U.S. Pat. No. 5,902,236, to Iversen, shows a tissue electrode for both monitoring tissue electrical activity and for stimulating that tissue. The electrode is designed to be inserted subdurally. The electrode itself is generally either a rhombus or a half rhombus in shape.

U.S. Pat. No. 5,938,689, to Fischell et al., shows a configuration of electrodes for stimulation of brain tissue. Generally the device includes a configuration of electrodes having at least one electrode on the brain surface and at least one additional electrode located deep within the tissue of the brain. Each electrode includes its own lead, as is typically the practice.

U.S. Pat. No. 6,006,124, to Fischell et al., shows a variety of ways of placing electrodes subdurally.

U.S. Pat. No. 6,024,702, shows an implantable electrode assembly made using a flexible printed circuit base. The non-conducting backing material is preferably a material such as Mylar or Silicone.

U.S. Pat. No. 6,094,598, to Elsberry et al., shows a method and a device for treatment of specific neural disorders resulting in abnormal motor response, by means of an implantable signal generator and electrode in an implantable pump and catheter. The various forms of the electrodes which are implantable in the brain. Various configurations for the implantable electrodes are shown in FIGS. 12–17.

None of the cited documents describes the devices and procedures claimed herein.

SUMMARY OF THE INVENTION

This invention deals with a combination lead having multiple electrodes configured both to provide extradural somatosensory electrical stimulation to an electrically sensitive region of a human body and to provide intracranial electrical stimulation to the brain. The combination lead is made up of an elongate member having a distal end that preferably is round or flattened in cross-section. The lead also has a proximal end. At least one distal electrode is located relatively distally of the proximal somatosensory electrode on said elongate member for providing electrical stimulation to said human brain. At least one somatosensory stimulation electrode is located relatively more proximal with respect to the distal electrode(s) on said elongate member and is further situated on said elongate member to provide electrical stimulation extradurally to said electrically sensitive region of a human body when said distal electrode(s) are in contact with said human brain. A plurality of contacts (generally as a female socket or male protuberance for connecting with another junction device) is located most proximal on said elongate member. The number of contacts in junction equals in number the sum of the distal brain electrodes plus said at least one somatosensory stimulation electrode. Each of the plurality of contacts is uniquely, electrically connected to a single distal electrode or somatosensory stimulation electrode. These contacts allow connection with the implanted neurostimulator central unit.

The somatosensory stimulation electrodes preferably have an area which is substantially larger than any one of the distal electrodes. Clearly, though, such is not a requirement. The distal electrodes may be bands on a circular cross-section elongate member or flat or protruding regions located on the flat distal end. Functionally speaking, the electrodes may be any shape that provides stimulatory contact with the tissue in question. The various electrodes may be made of a biocompatible metal or alloy, preferably platinum or platinum alloys, although many other metals, e.g., gold or palladium, may be suitable.

One variation of the invention includes a neurostimulator assembly for modifying an electrical activity in a human brain. The combination may comprise the inventive combination lead, an implantable neurostimulator central unit having at least a brain electrical activity sensor for sensing electrical activity in the brain, and a electrical signal source connectable to the somatosensory stimulation electrode. The electrical signal source is capable of initiating an electrical stimulation to the somatosensory stimulation electrode which is responsive to said brain electrical activity sensed by the brain electrical activity sensor. The implantable neurostimulator central unit may also include a non-responsive electrical signal source connectable to at least one of the distal electrodes.

Finally, the invention includes methods for treating a disorder in a human brain. The procedure maybe made up of the steps of detecting at least one brain electrical activity using the neurostimulator assembly and providing at least one electrical somatosensory stimulation signal to the somatosensory stimulation electrode. Alternatively, the stimulation may be used to provide a warning of abnormal EEG's (or potentially abnormal EEG's) or of a problem with the implanted system, to the patient. The method may further include the steps of applying non-responsive and/or responsive electrical brain stimuli to at least one of the distal electrodes. The electrical brain activity may be detected in a variety of sites, e.g., cortically or deep within the brain.

A BRIEF DESCRIPTION OF THE DRAWINGS

FIG. 1A shows, in cross section, the typical deep brain placement of the inventive lead in a patient, the situation of the extradural electrode(s), and the placement of the neurostimulator.

FIG. 1B similarly shows, in cross section, a surface placement of the inventive lead in the brain of a patient, the situation of the extradural electrode(s), and the placement of the neurostimulator.

FIGS. 2A and 2B show, respectively, side and top views of the surface variation of the inventive lead.

FIG. 2C is a partial cutaway of the inventive lead shown in FIGS. 2A and 2B and shows several structural features of the device.

FIG. 2D is a cross-sectional view of the inventive lead taken along line 2D—2D of FIG. 2B.

DESCRIPTION OF THE INVENTION

Figure 1A:
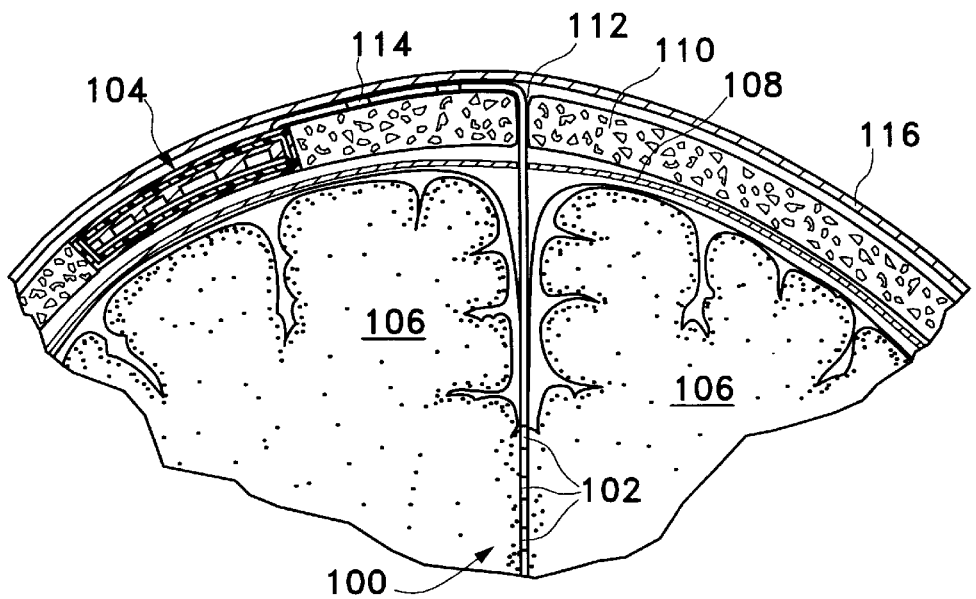

The inventive neurostimulator, its attendant inventive leads, and the processes of using them may include the generation and application of one or more of the following signals: a.) a generally "non-responsive" electrical stimulation (or stimulation signal) to the brain, b.) a "responsive" electrical stimulation to the brain, and c.) a somatosensory stimulation elsewhere to the body, preferably extradurally to the scalp or to the dura itself. Optionally, the process includes steps for detection of electrical activity of the brain, analysis of that activity for impending or existent epileptiform activity, and decision-making steps relating whether to initiate stimulation or to change the parameters of that stimulation.

By the term "stimulation", we mean an electrical signal applied to brain tissue or an electrical somatosensory input applied to the patient to elicit a response.

As used herein, "non-responsive" stimulation refers to the application of electrical therapy intended to lower the probability of a seizure occuring. The parameters (electrode or electrodes used, number of pulses, amplitude, pulse to pulse interval, duration of pulses, etc.) of the non-responsive stimulation, or the application of the non-responsive stimulation may be set or varied as a result of the detection of signals from the patient's body including the nervous system and brain or set by a physician.

As used herein, "responsive" stimulation refers to the application of electrical therapy in response to the detection of an electrographic (or some other) event indicating an impending or existent seizure. The electrographic event may be the beginning of an electrographic seizure, epileptiform activity, or other features of the EEG that typically occur prior to a seizure. Other events may include motion detection, or external triggering.

As used herein, "somatosensory" stimulation refers to the application of one or more electrical signals to some region of the body capable of sensing the signal. The body region is typically extradural, i.e., outside of the dura layer surrounding the majority of the neural tissue. Preferred sites, because of their proximity, are the scalp and the dura layer itself. The somatosensory stimulation is also typically applied in response to the detection of an event indicating an impending or existent seizure as discussed just above.

As used herein, "seizure" may represent a behavioral seizure wherein clinical evidence of functional or cognitive manifestations of the seizure may be elucidated by testing the patient; or electrographic seizure which refers to abnormalities detectable on the EEG (whether from brain, scalp or other electrodes).

The term "epileptiform activity" refers to the manifestation on an EEG (cortical, depth, or scalp) of abnormal brain activity whether associated with clinical manifestations or not.

"Electrical stimulation" means the application of an electric field or electric current to biological tissue, "stimulation" means electrical or somatosensory stimulation.

Non-responsive Stimulation

The brain's electrical activity may be detected and analyzed to detect epileptiform activity or to detect such impending activity. If the epileptiform activity is present or impending, responsive brain stimulation or somatosensory stimulation may be initiated for the purpose of averting a seizure. Alternatively, somatosensory stimulation may be used to warn the patient of an increased probability of seizure so that the patient may take proactive action to limit risk or increase medication doses. The results of analysis of the epileptiform activity may also be used to modify the parameters of the non-responsive stimulation to optimize the suppression of seizures of other undesirable neurological events.

The parameters (electrode or electrodes used, number of pulses, amplitude, frequency, duration of pulses, etc.) of the responsive brain stimulation or somatosensory stimulation may be varied. The variation of the parameters may be based either upon a preprogrammed sequence or based upon some characteristic of the detected epileptiform activity. Application of the responsive or somatosensory stimulation may be temporally paused or the amplifier blanked during that stimulation to allow analysis of the electrical activity of the brain and thence determine whether the stimulation has had its desired effect. Readjustment of the parameters of the stimulation may be repeated as long as it is advantageous in terminating the undesirable epileptiform activity.

In addition to desirably providing for responsive or somatosensory stimulation delivered upon detecting an indication of epileptiform activity, this invention optionally includes the steps of decreasing the incidence of seizures using non-responsive stimulation. The use of non-responsive stimulation in conjunction with responsive brain stimulation or somatosensory stimulation can be used to optimize the control of seizures by providing a multifrontal attack to reduce the incidence of seizures and to terminate any breakthrough seizures which may occur while using somatosensory stimulation as a primary responsive stimulation or as an indication of responsive therapy.

In one variation, the procedure and device provides neurostimulation that is believed to modulate neurotransmitter levels or provide neural desynchronization in the brain resulting in a reduction of seizure incidence. Appropriate use of non-responsive neurostimulation may also be used to reduce the risk of kindling, a phenomenon demonstrated in animal models in which stimulation may make the neural tissue more prone to epileptogenesis. In any event, any epileptiform electrical activity that may occur may be terminated by use of somatosensory or responsive brain stimulation. As will be discussed below, the non-responsive stimulation and the responsive brain stimulation may be delivered from the same electrode, but preferably are delivered from one or more separate electrodes connected to the same implantable neurostimulator. The location of the electrode for the responsive brain stimulation is preferably near the epileptogenic focus. The electrode for non-responsive stimulation may be located in a deep brain structure such as the thalamus, hippocampus, amygdala or perhaps in contact with the cerebellum, but need not be. The electrode for non-responsive stimulation may be located in brain tissue and accessed through a burr-hole in the skull.

The non-responsive stimulation desirably is set in a manner that maximizes inhibitory effects and reduces the incidence of seizures. The stimulation typically is made up of low intensity, short duration pulses. Pulsing frequencies of from 0.1 to 200 Hz, preferably at a rate from about 20 to 150 Hz., may be applied for durations between less than a second and up to 15 minutes or more. This also reduces the likelihood of kindling. The parameters for application of the non-responsive stimulation may be varied according to circadian rhythms. In particular, for some patients, it will be advantageous to alter the stimulation patterns before or during normal sleep times to avoid disrupting sleep patterns, particularly REM sleep.

Responsive Brain Stimulation

As noted above, the responsive brain stimulation may be initiated when an analysis of the brain's electrical activity shows an impending or extant neurological event, such as epileptiform activity. To detect such activity reliably while the non-responsive stimulation is in progress often presents challenges. In some cases, the level of non-responsive stimulation is set at a low enough level, and the sensing electrodes are physically far enough away, that the stimulation does not interfere with detection of brain activity. The use of closely spaced electrodes for either non-responsive stimulation and detection, or both, is helpful in this regard. Often however, it is necessary to take measures to keep the non-responsive stimulation from interfering with detection of brain activity. One method for doing that is to "blank" the detection amplifier (or other detecting circuit component) during the pulse output of the non-responsive stimulation. If that is not effective in eliminating the interference, it may be necessary to periodically pause application of the non-responsive stimulation to allow detection of brain activity.

The typical responsive brain stimulation pulses are biphasic in nature and have a duration of 0.025 to 0.50 milliseconds per phase. A blanking signal slightly precedes and lasts longer than the stimulation pulses to assure that no stimulation artifact disturbs the measurement. The overall duration of the blanking time desirably is typically 1 to 5 milliseconds.

As noted above, another variation of the step for detecting the electrical activity of the brain amidst intermittent instances of stimulation involves (instead of blanking the input to the amplifier) pausing the various electrical stimulation signals for a discrete period, during which the measurement of neuroelectrical activity may be made.

Somatosensory Stimulation

Somatosensory stimulation is generally responsive in nature and applied to a portion of the human body which is capable of detecting the electrical impulse or signal applied to that body location. Preferably for this invention, the somatosensory stimulation is applied extradurally to the underside of the scalp or to the dura itself, most preferably using the inventive devices described elsewhere herein. The somatosensory stimulation, in conjunction with the physical size of the one or more somatosensory electrodes, should provide a electrical/physical input to the patient which is detectable to the patient and which is of sufficient strength, duration, over an area that has sufficient neural sites to assist in minimizing or modifying epileptiform activity. Consequently, current density at the somatosensory electrode or electrodes is believed to be an important parameter. The passive electrical parameters of human tissue vary from person-to-person and, indeed, within a single individual. Nevertheless, the following are considered to be indicative of effective somatosensory impulses and related parameters.

The impedance of the tissue in the neighborhood is often near 1000 ohms. Somatostimulation currents in the range of 0.5 to 20 mA may be desired and 1–10 mA. are also effective. Patients often can detect currents as low as 2–3 mA. At such currents, voltages of 0.5–20 volts and preferably 1–10 volts are then set. Similarly if the tissue impedance is higher or lower, the voltage would be adjusted to compensate.

Desirably, the somatosensory impulses are desirably pulses having a pulse width between 0.1 and 10 ms. (per phase in a biphasic charge-balanced pulse), desirably between 0.1 and 0.5 ms., most preferably near 0.3 ms. The pulse rate desirably is less than about 120 Hz, preferably 30–50 Hz.

Monitoring and Responsive Activity

In any event, should pending or existent epileptiform electrical activity be detected in some part of the brain during a monitoring period, preferably the somatosensory stimulation is initiated and, if ineffective, the responsive brain stimulation then initiated. It is within the scope of this invention that the somatosensory electrodes be used as "return electrodes" during neural stimulation to the distal brain electrodes or even during monitoring. In this way, the electrical brain stimulus may also act as somatosensory stimuli as it returns to the somatosensory electrodes. The somatosensory electrodes may also be used as monitoring or sensing electrodes as appropriate. In any case, if non-responsive stimulation is occurring, it may continue or be cessated. Later, the non-responsive stimulation, somatosensory stimulation, and the responsive brain stimulation may be are then temporally paused for monitoring to determine whether epileptiform activity has ceased. The responsive brain stimulation, somatosensory stimulation, and non-responsive stimulation may be paused simultaneously, or one may ceased individually. Of course, as is discussed below, if the responsive stimuli are re-initiated, they may be re-initiated either with or without being modified in some fashion There are several methods of predicting an impending seizure. Many are discussed in U.S. patent application Ser.

No. 09/543,450, filed Apr. 5, 2000, entitled MULTIMODAL NEUROSTIMULATOR AND PROCESS OF USING IT, the entirety of which is incorporated by reference. The methods include monitoring or detection of EEG synchronization from multiple brain sites and of a shift in the energy spectrum. A preferred monitoring scheme is detection of a shift in phase-space parameters. When such a shift occurs, it indicates that a seizure is likely to occur soon, e.g., within the next two to sixty minutes. Under such circumstances, the inventive neurostimulation process may variously modify the non-responsive parameters of stimulation and initiate the responsive forms of stimulation. The stimulation changes the underlying dynamics of the brain which results in a reduced likelihood of the impending seizure occurring. Of course, if a seizure occurs, or if the monitoring scheme determines that a seizure is imminent in less than a minute, the responsive or somatosensory stimulation may be applied to terminate it.

As noted above, it is within the scope of this invention to vary the specific electrode used and the parameters (duration, amplitude, number, pulse to pulse interval is varied within a burst, number of pulses in a burst, etc.) of the pulses or of the burst, for the various responsive and non-responsive modes of stimulation. Varying the pulse-to-pulse interval within a burst is highly desirable in de-synchronizing neuronal activity. The range of pulse-to-pulse intervals may be varied randomly or changed in a systematic fashion, such as incrementing or decrementing the pulse to pulse interval within a burst.

Shorter duration pulses (on the order of 50 to 150 microseconds) tend to directly depolarize smaller diameter nerve cells. Longer pulses (100 to 500 microseconds) depolarize larger diameter nerve cells. By varying pulse amplitude, the individual pulses may be tailored directly to depolarize different neural tissue. Lower amplitude pulses directly depolarize tissue in the immediate vicinity of the electrode; higher amplitude pulses directly depolarize tissue both near the electrode and at some distance from the electrode. By varying the amplitude of the pulses within a burst, local tissue can be depolarized at a higher rate than tissue somewhat distant from the electrode.

Since the tissue disposed near an electrode may have highly variable anatomy, it is anticipated that any or all of the parameters described (pulse to pulse interval, pulse amplitude, the use of hyperpolarizing pulses, pulse width, etc.) may be varied alone or in combination to optimize the ability of a burst to terminate epileptiform activity in the brain while improving the safety of the burst by reducing the likelihood of inducing epileptiform activity or generalizing such pre-existing activity.

In addition to producing bursts having pulse intervals having pre-set or absolute time increments, this procedure may be used to set the pulse-to-pulse interval based upon the detected temporal interval of the epileptiform activity as sensed by the electrodes detecting the brain electrical activity. In this mode of operation, the rate of the sensed epileptiform activity is detected and measured. The rate of the detected activity is used to modulate the rate, or the average rate, of the burst used to terminate the epileptiform activity.

Leads

FIG. 1A shows, in cross-section, one desirable typical placement—the deep brain placement between the hemispheres of the brain—of the inventive lead (100). Not shown, but also desirable, is a variation in which the electrode for non-responsive stimulation is located within brain tissue, but not between the hemispheres, and accessed through a burr-hole in the skull. The lead (100) is an elongated member that includes at least one distal electrode (102). The distal electrodes (102) may be used both to detect neural electrical activity and to stimulate the brain. Each of the distal electrodes (102) is electrically connected to a unique wire or conductor within the lead (100) which ultimately terminates in the neurostimulator central unit (104). As shown in the FIG. 1A, the distal electrodes (102) may be placed deep within the brain between the hemispheres (106). The lead (100) extends proximally through the dura layer (108) surrounding the brain and through the skull (110) often through a burr hole (112) provided for that access. Central to this invention is the presence of at least one somatosensory electrode (114) preferably located beneath the scalp (116) adjacent the neurostimulator central unit (104). The lead (100) is electrically connected (as discussed below) to the neurostimulator central unit (104). The somatosensory electrode (114) is also preferably connected via a unique wire to the neurostimulator central unit (104). Although only one somatosensory electrode (114) is shown in the Figures for the sake of simplicity, the use of multiple somatosensory electrodes is suitable.

Figure 1B:
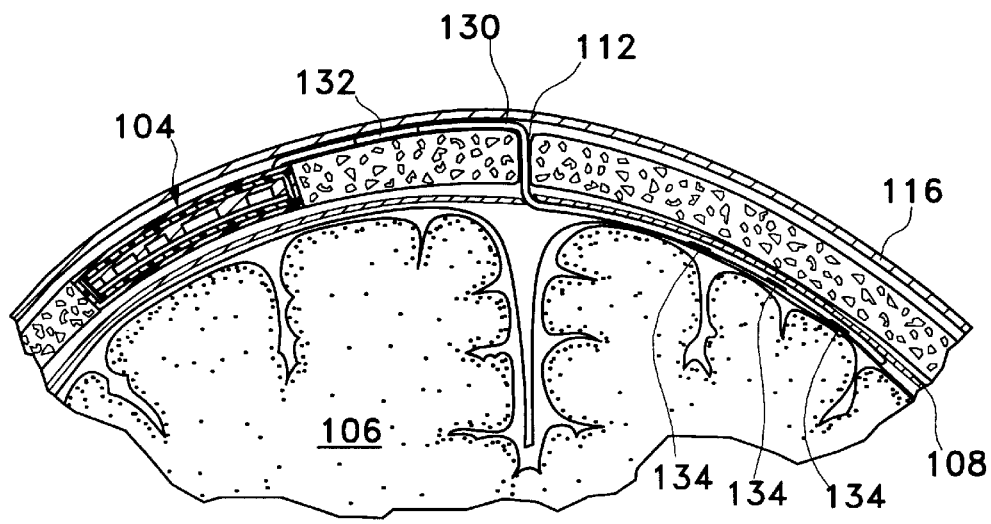

FIG. 1B shows a variation of the placement of the inventive leads—a surface placement—generally using the variation of the lead shown in FIGS. 2A, 2B, 2C, and 2D. Again, the lead (130) extends proximally through the dura layer (108) and through the skull (110) desirably through a burr hole (112) provided for that access. The at least one somatosensory electrode (132) is again preferably located beneath the scalp (116) adjacent the neurostimulator central unit (104). The lead (130) is electrically connected to the neurostimulator central unit (104).

FIGS. 2A, 2B, and 2C show, respectively, side, top, and cross-sectional views of the variation of the lead (100) shown in FIG. 1A. The distal end (138) of the lead (100) includes at least one stimulator electrode (102). A multiplicity of electrodes (102) is desirable if the situation of the patient makes it so. In any case, the distal stimulation electrodes (102) are preferably constructed as shown in FIG. 2D. The distal stimulation electrode (102) itself is preferably a ring in the outer surface of the elongate tubing making up the distal shaft (138). In turn, the electrode (102) is in electrical contact with a longitudinal wire (142) which extends to a contact (140) at the proximal end of the lead (100). Longitudinal wire (142) is also shown in FIG. 2C. Longitudinal conductors or wires (142) may be of any of a variety of configurations, e.g., discrete wires or printed circuit type conductors. Preferably, the longitudinal conductors or wires (142) are spirally configured along the axis of the lead (100) until reaching the proximal end (142) and the connector contacts (140).

The shaft of the lead (100) preferably is hollow having a lumen (150) to permit use of a stylet for a measure of rigidity during installation. The shaft is preferably made up of a comparatively stiffer inner tubing member (152) of, e.g., polyimides, polyamides (e.g., Nylon), high density polyethylene (HDPE), polypropylene, polycarbonate, or the like. Polyimide polymers are preferred. Similarly, the shaft preferably has a comparatively softer outer tubing member (154) of, e.g., a Silicone or a suitable elastomeric polymer. We prefer to have a disjunct or discontinuation of the inner tubing member (152) distal of the proximal somatosensory electrode (114) to allow the lead to flex or bend at the burr hole (110) as shown in FIG. 1A.

Finally, the proximal end has a number of contacts (140) that, as mentioned above, are electrically tied to the various electrodes, both the distal stimulation electrodes (102) and the proximal somatosensory electrode (114). The somatosensory electrode (114) is preferably near to the contacts (140). Each of the electrodes (102, 114) and the contacts (140) are preferably of a biocompatible metal such as one selected from the Noble Group of metals, but preferably comprises palladium, platinum, or gold and their alloys. Preferred is a platinum-iridium alloy.

Generally, the length of lead (100) is between 25 and 50 cm, preferably 25–45 cm. The diameter is typically in the range of 0.5–2 mm, preferably in the range of 1.0–1.3 mm. The somatosensory electrode (114) preferably has an axial length between 0.5–10 mm depending upon the various factors discussed above with relation to stimulation current density. The distance between the distal end of the somatosensory electrode (114) and the most proximal of the distal stimulation electrodes (102) is usually about 1.5 to 10.0 cm. Any excess length may be coiled or re-oriented out of the way. Finally, the distal stimulation electrodes (102) may be 0.5–3.0 mm., preferably 1.0–1.5 mm, with a pitch of 7.5 to 12.5 mm, preferably about 10 mm.

Figure 3A:
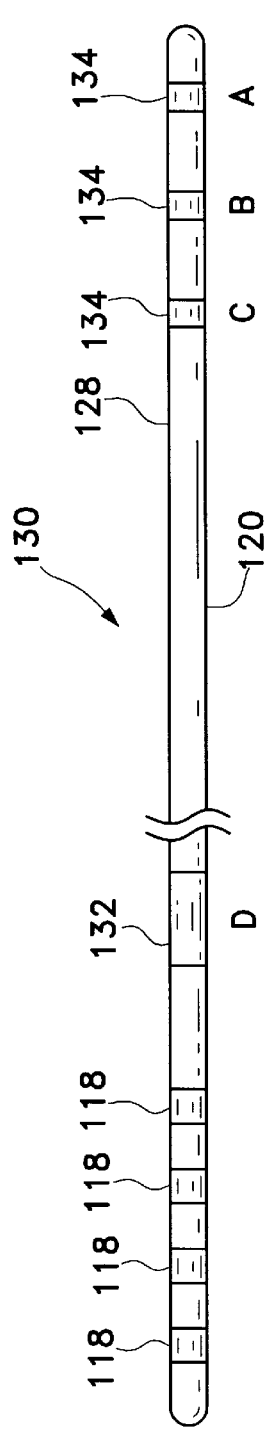
FIGS. 3A and 3B show, respectively, side and top views of the deep brain variation of the inventive lead.
Figure 3B:
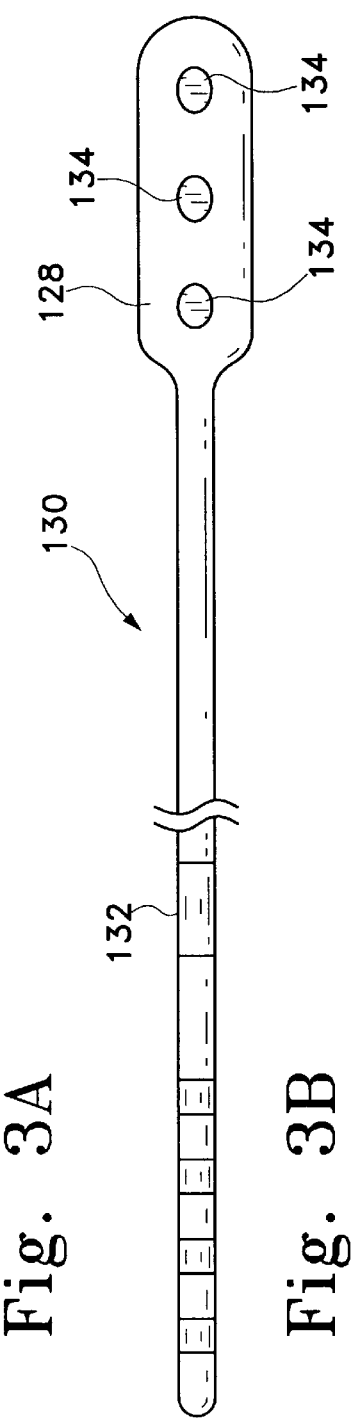
Figure 3C:
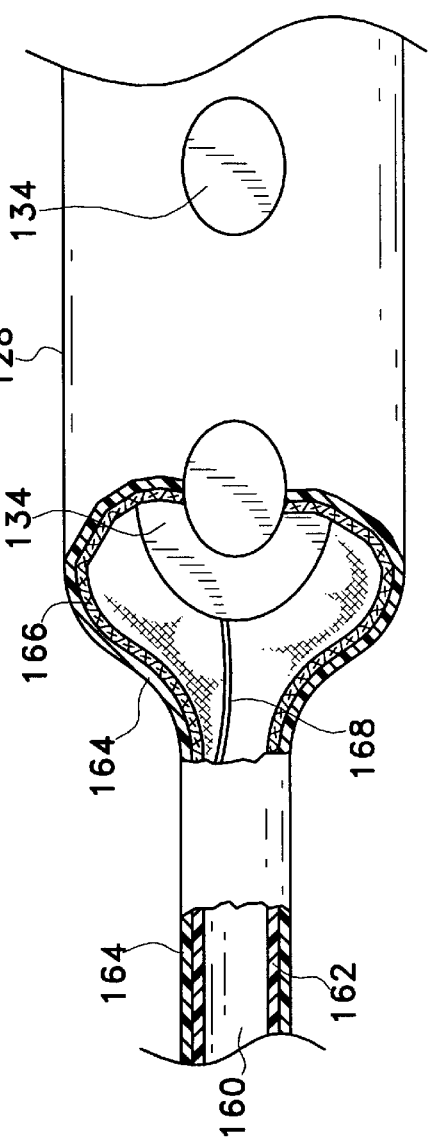
FIG. 3C is a partial cutaway top view of the inventive lead.

FIGS. 3A, 3B, and 3C show, respectively, side, top, and partial cutaway views of the variation of the lead (100) shown in FIG. 1B. In general, this variation differs from that shown in FIGS. 2A, 2B, 2C, and 2D in that it is for use on the surface of the brain rather than in the deep brain position. Near the distal end (128) is at least one distal electrode (102) that is preferably uniquely electrically connected to a like number of connector sites or contacts (118) located proximally on that lead (130). The materials of construction and the various typical dimensions are the same as those for the other variations. The overall length may be less because the placement of the device is usually closer to the neurostimulator central unit (104) as shown in FIG. 1B.

As is shown in FIG. 3B, the distal end (128) of the lead (100) may be broader or paddle-shaped to support the individual distal electrodes (134). As is shown in FIG. 3C, the configuration of this variation of the lead (100) is similar in many aspects to the variation discussed earlier. The may be a lumen (160) to allow use of a comparatively rigid stylet during placement of the device. A comparatively stiffer inner tubing member (162) may be used. An outer covering (164) that is integral over the distal end of the device is desired. Preferably, the outer covering (164) comprises an elastomeric, biocompatible polymer such as those discussed above. A Silicone polymer is preferred. These materials may be molded in place. In this variation, the distal electrodes (134) are partially covered by the outer covering (164). We typically use a disk-shaped distal electrode (134) having a diameter of about 5–7 mm although only 3–5 mm of the electrode is exposed.

Further, it is desirable to reinforce the distal end (128) with a fabric (woven or unwoven) (166) to provide structure to the distal paddle portion. Finally, FIG. 3C shows a wire or conductor (168) connected to one of the distal electrodes (134). The conductor (168) passes interior to (or within) the outer covering (164) and terminates at the contacts (118) as shown in FIGS. 3A and 3B.

Implantable Neurostimulator

Figure 4:
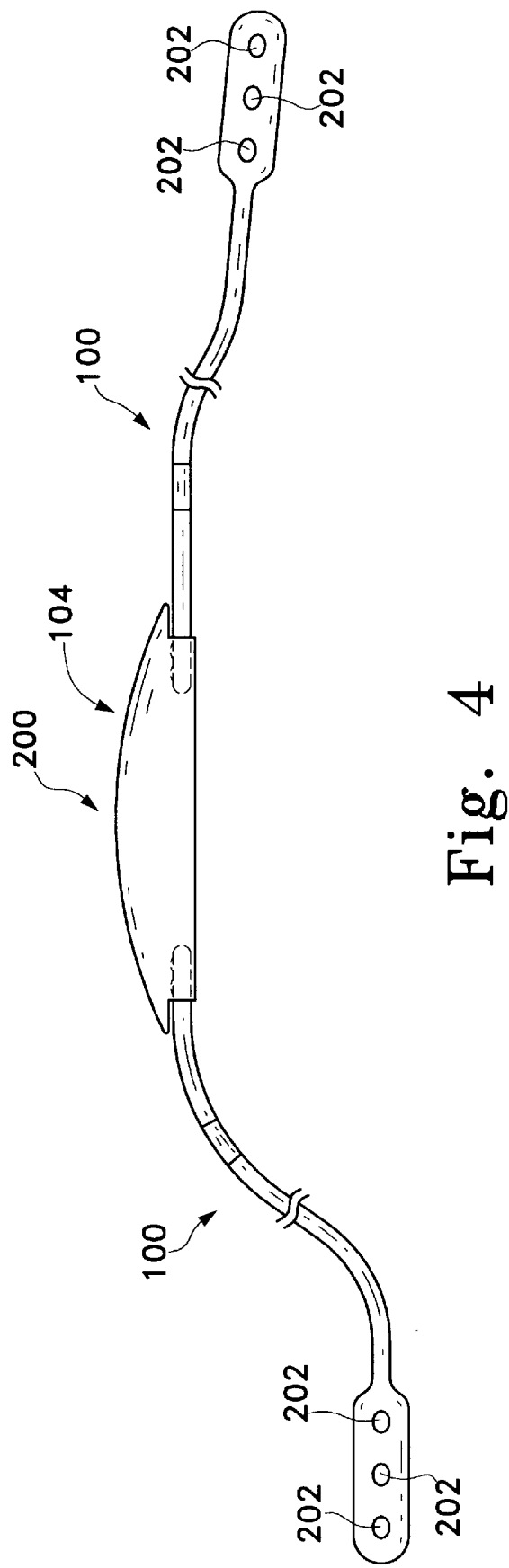
FIG. 4 is a depiction of one variation of the inventive neurostimulator having multiple electrodes.

As is shown in FIG. 4, one variation of the inventive device includes a neurostimulator central unit (104) and at least one inventive lead (100). The neurostimulator central unit (104) includes the necessary circuitry, e.g., A/D converters, filters, central processing unit(s), digital processing circuits, blanking circuits, power supplies, batteries, signal generators, etc., and programming configured and adapted to perform the steps listed above. Specifically the neurostimulator central unit (104) desirably is as shown in FIG. 4 and is shaped in such a way that it conforms to the shape of the skull as shown in FIGS. 1A and 1B, although it need not be so. The neurostimulator central unit (104) may contain a non-responsive electrical stimulation source, a responsive brain stimulation source (particularly where both sources may be the same circuit operated in two different modes), a somatosensory stimulation source, and devices for detecting epileptiform activity and for initiating and for terminating the various stimuli.

The neurostimulator assembly (200), as shown in FIG. 4, may include a neurostimulator central unit (104) and one or more neurostimulator electrodes (202), and a responsive electrical neurostimulator leads (100). A detailed embodiment of the neurostimulator central unit (104) may be found in U.S. Pat. No. 6,016,449. The various necessary connectors, leads, and supporting components are also included.

Although preferred embodiments of the invention have been described herein, it will be recognized that a variety of changes and modifications can be made without departing from the spirit of the invention as found in the appended claims.

I claim as my invention:

1. A combination lead having multiple electrodes configured both to provide extradural electrical stimulation to an electrically sensitive region of a human body and to provide intracranial electrical stimulation to the brain, comprising
   a.) an elongate member having a distal and a proximal end,
   b.) at least one or more electrodes located relatively distally on said elongate member for at least one of providing electrical stimulation to said human brain or sensing electrical activity in said brain,
   c.) at least one somatosensory stimulation electrode located relatively more proximal with respect to said distal at least one or more electrodes on said elongate member and further placed on and situated on said elongate member to provide electrical stimulation extradurally to said electrically sensitive region of a human body when said at least one distal electrode is in contact with said human brain, and
   d.) at least one contact for electrical connection to an implanted implantable neurostimulator central unit, said at least one contact located most proximal on said elongate member and equaling in number the sum of the at least one distal electrodes plus said at least one somatosensory stimulation electrode and each at least one contact is uniquely, electrically connected to a one of said at least one distal electrodes or said at least one somatosensory stimulation electrode.

2. The combination lead of claim 1 wherein the at least one somatosensory stimulation electrode has an area which is substantially larger than any one of the distal at least one or more electrodes.

3. The combination lead of claim 2 wherein the at least one somatosensory stimulation electrode is a single electrode.

4. The combination lead of claim 1 wherein the distal end of said elongate member is flat and said distal at least one or more electrodes are located on said flat distal end.

5. The combination lead of claim 4 wherein the distal at least one or more electrodes are substantially flat.

6. The combination lead of claim 1 wherein said elongate member is substantially cylindrical.

7. The combination lead of claim 6 wherein the distal at least one or more electrodes are substantially ring-shaped.

8. The combination lead of claim 1 wherein the at least one somatosensory stimulation electrode and the distal at least one or more electrodes are comprised of a biocompatible metal or alloy.

9. The combination lead of claim 8 wherein the biocompatible metal or alloy is selected from the Noble Metals and alloys of those metals.

10. The combination lead of claim 9 wherein the biocompatible metal or alloy is an iridium-platinum alloy.

11. An neurostimulator assembly for modifying an electrical activity in a human brain, comprising in combination:
   a.) the combination lead of claim 1, and
   b.) an implantable neurostimulator central unit having at least
      i.) at least a brain electrical activity sensor for sensing electrical activity in said brain,
      ii.) at least a electrical signal source connectable to said at least one somatosensory stimulation electrode, said electrical signal source initiating an electrical stimulation to said at least one somatosensory stimulation electrode which is responsive to said brain electrical activity sensed by said brain electrical activity sensor.

12. The neurostimulator assembly of claim 11 wherein the implantable neurostimulator central unit further comprises a non-responsive electrical signal source connectable to at least one of said distal at least one or more electrodes.

13. The neurostimulator assembly of claim 11 wherein the implantable neurostimulator central unit further comprises a responsive electrical signal source connectable to at least one of said distal plurality of electrodes, said responsive electrical signal source initiating an electrical stimulation to at least one of said distal at least one or more electrodes which is responsive to said brain electrical activity sensed by said brain electrical activity sensor.

14. A method for treating a disorder in a human brain, comprising the steps of:
   a.) detecting at least one brain electrical activity of said brain using the neurostimulator assembly of claim 11, and
   b.) providing at least one somatosensory stimulation to said at least one somatosensory stimulation electrode, which responsive brain stimulation is responsive to said at least one brain electrical activity.

15. The method of claim 14 further comprising the step of applying a non-responsive electrical stimulation to at least one of said distal electrodes.

16. The method of claim 14 further comprising the step of applying a responsive electrical stimulation to at least one of said distal electrodes, said responsive electrical stimulation being responsive to said brain electrical activity sensed by said brain electrical activity sensor.

17. The method of claim 15 further comprising the step of applying a responsive electrical stimulation to at least one of said distal plurality of electrodes, said responsive electrical stimulation being responsive to said brain electrical activity sensed by said brain electrical activity sensor.

18. The method of claim 16 further comprising the step of pausing said at least one non-responsive electrical stimulation or said somatosensory electrical stimulation during the step of providing said at least one responsive brain stimulation.

19. The method of claim 16 wherein multiple responsive electrical stimulations are independently applied to multiple distal electrodes.

20. The method of claim 14 wherein said at least one brain electrical activity is detected cortically.

21. The method of claim 14 wherein said at least one brain electrical activity is detected at a depth within the brain.

* * * * *